United States Patent [19]

Kim et al.

[11] Patent Number: 5,434,320

[45] Date of Patent: Jul. 18, 1995

[54] PROCESS FOR PREPARING DICHLOROFLUOROETHANE AND CHLORODIFLUOROETHANE

[75] Inventors: Hong G. Kim; Hoon S. Kim; Young S. Kwon; Kun Y. Park, all of Seoul, Rep. of Korea

[73] Assignee: Korea Institute of Science and Technology, Seoul, Rep. of Korea

[21] Appl. No.: 178,795

[22] Filed: Jan. 6, 1994

[51] Int. Cl.$^6$ .............................................. C07C 17/08
[52] U.S. Cl. ..................................................... 570/164
[58] Field of Search ........................................ 570/164

[56] References Cited

U.S. PATENT DOCUMENTS

| | | |
|---|---|---|
| 3,833,676 | 9/1974 | Ukaji et al. . |
| 4,258,225 | 3/1981 | Feiring . |
| 4,849,555 | 7/1989 | Cheminal et al. . |

FOREIGN PATENT DOCUMENTS

| | | | |
|---|---|---|---|
| 0402626 | 12/1990 | European Pat. Off. ............. | 570/184 |
| 2137806 | 2/1972 | Germany ............................ | 570/164 |
| 58-217403 | 12/1983 | Japan . | |
| 59-46211 | 11/1984 | Japan . | |
| 2152935 | 6/1990 | Japan . | |
| 3153641 | 7/1991 | Japan ................................... | 570/164 |
| 917847 | 5/1991 | Rep. of Korea . | |

*Primary Examiner*—Alan Siegel

*Attorney, Agent, or Firm*—Oblon, Spivak, McClelland, Maier & Neustadt

[57] ABSTRACT

This specification discloses a process for preparing 1,1-dichlorofluoroethane (HCFC-141b) and 1-chloro-1,1-difluoroethane (HCFC-142b) from 1,1,1-trichloroethane and hydrogen fluoride which is capable of increasing reaction conversion and selectivity of the reaction products, HCFC-141b and HCFC-142b. According to the process of the invention, HCFC-142b, one of the reaction products, which has high solubility in both hydrogen fluoride and 1,1,1-trichloroethane, in the liquid phase reaction system is maintained at above 20 mole % relative to 1,1,1-trichloroethane. Therefore, the solubility of HF in the organic phase is remarkably enhanced, and the reaction of HF with 1,1,1-trichloroethane or vinylidene chloride is well promoted. Furthermore, the resident time of the reactant in the reaction vessel is shortened and thus the formation of tars is considerably prevented. According to the process of the invention, the hydrogen chloride produced during the fluorination is removed from the top of the reaction vessel, and the reaction mixture, except a minor portion of the lower boiling chlorofluorocarbons, are continuously recovered from the reactants in the bottom of the vessel, and then the desired products are separated from the reaction mixture with recycling the unreacted reactants and an effective amount of 1,1-difluoro-1-chloroethane into the vessel.

5 Claims, No Drawings

PROCESS FOR PREPARING DICHLOROFLUOROETHANE AND CHLORODIFLUOROETHANE

BACKGROUND OF THE INVENTION

1. Field of the Invention

The present invention relates to a process for preparing 1,1-dichlorofluoroethane (HCFC-141b) and 1-chloro-1,1-difluoroethane (HCFC-142b) from 1,1,1-trichloroethane and hydrogen fluoride. More particularly, the present invention relates to a new process for preparing HCFC-141b and HCFC-142b, which is capable of increasing the reaction conversion and selectivity of the reaction products, HCFC-141b and HCFC-142b. In the process according to the invention, a known, non-catalytic reaction of 1,1,1-trichloroethane with hydrogen fluoride is employed.

2. Description of the Prior Art

HCFC-141b and HCFC-142b have remarkably lower ozone depletion potentials than chlorofluorocarbons which are used as foaming agents, refrigerants, and the like. HCFC-141b has outstanding physical properties for a polyurethane foaming agent and a cleaning solvent for electronic circuits. HCFC-142b is used as a refrigerating medium and a propellant for aerosols. Thus, recently, demands of these materials tend to be gradually increasing.

In general, it is known that HCFC-141b and HCFC-142b are simultaneously obtained when reacting 1,1,1-trichloroethane with hydrogen fluoride in the presence or in the absence of a catalyst.

Methods of preparing HCFC-141b and HCFC-142b in the presence of a catalyst are disclosed in Japanese Patent Publication 59-46211 wherein an antimony halide catalyst is employed, and in U.S. Pat. No. 4,258,225 wherein a thallium halide is used. In these methods, chlorine must be periodically supplied into the reaction system because of the gradual degradation of the catalyst; this may cause undesired side-reactions formed.

In U.S. Pat. No. 4,849,555, use of perfluoroalkanesulfonic acid as a catalyst is disclosed. This method is not practical because it requires an expensive catalyst and a high reaction pressure of above 30 atm.

Korean Laid-Open Patent Publication 91-7847 discloses a method of manufacturing only HCFC-142b using an antimony halide catalyst.

In order to avoid the formation of high molecular weight by-products (in most cases, products having at least 4 carbon atoms) and deactivation of the catalysts, non-catalytic processes have been suggested. For example, U.S. Pat. No. 3,833,676 proposes a method of using an excess of hydrogen fluoride in the absence of a catalyst; however, this method suffers from the problems involved in the recovery and recycling of the excess hydrogen fluoride.

In Japanese Laid-Open Patent Publication 2-152935, the amount of hydrogen fluoride used is significantly reduced, but the reaction time is extended considerably due to the low reaction rate.

Further, Japanese Laid-Open Patent Publication 58-217403 discloses in detail the way to recover hydrogen fluoride during the production of HCFC-141b and HCFC-142b from 1,1,1-trichloroethane, and to solve the problem of the formation of tars.

However, the prior art methods mentioned above failed to meet the requirements for increasing reactivity and minimizing the formation of the tars.

In general, synthesis of HCFC-141b and HCFC-142b from 1,1,1-trichloroethane and hydrogen fluoride is carried out stepwise in accordance with the following reactions:

<Cl-F exchange reaction>

$$CH_3CCl_3 + HF \rightarrow CH_3CCl_2F + HCl \quad (1)$$

$$CH_3CCl_2F + HF \rightarrow CH_3CClF_2 + HCl \quad (2)$$

<Elimination of HCl and addition of HF>

$$CH_3CCl_3 \rightarrow CH_2=CCl_2 + HCl \quad (3)$$

$$CH_2=CCl_2 + HF \rightarrow CH_3CCl_2F \quad (4)$$

$$CH_3CCl_2F \rightarrow CH_2=CClF + HCl \quad (5)$$

$$CH_2=CClF + HF \rightarrow CH_3CClF_2 \quad (6)$$

The reaction of 1,1,1-trichloroethane with hydrogen fluoride can be classified into two reaction categories; one is to substitute the fluorine atom for the chlorine atom (Reactions (1) and (2)), and the other is elimination of hydrogen chloride and subsequent addition of hydrogen fluoride into the resulting olefins (Reactions (3)–(6)).

In the case of a liquid phase reaction employing an antimony halide catalyst, activity of the catalyst tends to gradually decrease as the reaction proceeds since Sb (V) is reduced into Sb (III). Deactivation of catalyst can be prevented by adding chlorine (Cl$_2$) into the reaction system. However, it has been found that side-products are formed by the following reactions of the residual, unsaturated compounds (such as, CH$_2$=CCl$_2$ and CH$_2$=CClF) with added chlorine.

$$CH_2=CCl_2 + Cl_2 \rightarrow CH_2Cl-CCl_3 \quad (7)$$

$$CH_2=CClF + Cl_2 \rightarrow CH_2Cl-CCl_2F \quad (8)$$

On the other hand, Cr- and Al-based catalysts are known as catalysts for the vapor phase reaction. In this reaction, however, there are problems that a high reaction temperature (such as 300° to 400° C.) is required, and the possibility of formation of over fluorinated compound, 1,1,1-trifluoroethane (CH$_3$CF$_3$, HFC-143a) is undesirably increased.

SUMMARY OF THE INVENTION

It is a main object of the present invention to provide a process for preparing HCFC-141b and HCFC-142b, which is capable of increasing conversion and selectively by employing a non-catalytic reaction of 1,1,1-trichloroethane with hydrogen fluoride.

DETAILED DESCRIPTION OF THE INVENTION

We, the inventors, have recognized that the main reason for the formation of tars in the non-catalytic fluorination of 1,1,1-trichloroethane is that vinylidene chloride (CH$_2$=CCl$_2$), which is formed by dehydrochlorination of 1,1,1-trichloroethane, is polymerized when a relatively small amount of hydrogen fluoride is used. We have unexpectedly found that HCFC-142b, one of the reaction products, has good solubility in both hydrogen fluoride and 1,1,1-trichloroethane, and that the solubility of HF in the organic phase is remarkably enhanced by the presence of HCFC-142b. We have further found that the reaction of HF with 1,1,1-trichloroethane or vinylidene chloride is greatly promoted by maintaining the amount of HCFC-142 at least over 20 mole % relative to 1,1,1-trichloroethane. Furthermore, we have discovered that the resident time of the reactants in the reaction vessel is shortened; thereby, the formation of tars is prevented by a process which comprises removing hydrogen chloride from the top of the reaction vessel, recovering continuously the reaction mixture, except lower boiling chlorofluorocarbons, from the bottom of the vessel, separating the reaction products from the mixture in following distillation columns, and then recycling the unreacted reactants and an effective amount of 1,1-difluoro-1-chloroethane into the vessel.

The non-catalytic reaction of 1,1,1-trichloroethane with hydrogen fluoride may be carried out at a temperature ranging from 50° to 160° C. However, at temperatures lower than 60° C., the reaction rate is so slow that large reaction vessels for industrial processes are required. If the reaction temperature exceeds 120° C., many problems, such as risks of partial dehydrochlorination of the reaction products and formation of the perfluorinated compound HFC-143a, may occur. Thus, it is preferred to carry out the reaction at a temperature ranging from 60° to 120° C.

The molar ratio of hydrogen fluoride to feeding materials ranges from 1 to 10, and preferably, from 3 to 8. The feeding ratio of HCFC-142b relative to 1,1,1-trichloroethane ranges from 20 to 100 mole %, and preferably, from 30 to 70 mole %. The concentration of HCFC-142b in the organic phase is maintained at least more than 20 mole %, and preferably, from 30 to 50 mole %. Either HCFC-142b purified or unpurified may be used. The unpurified HCFC-142b may be obtained from the course of producing and separating HCFC-141b and HCFC-142b.

The present invention may be carried out at any pressure. However, it is preferred to carry out the reaction at a pressure ranging from atmospheric pressure to 20 atm, and preferably, from 6 to 15 atm in order to effect post-treatments such as separation of the by-product, HCl.

The reaction vessel used is made of SS-316. The reaction product is analyzed by gas chromatography using a Krytox-143AC column.

DESCRIPTION OF THE PREFERRED EMBODIMENTS

The present invention will be illustrated in greater detail by way of the following examples. The examples are presented for illustration purposes only and should not be construed as limiting the invention which is properly delineated in the claims. In the Examples, mole % is represented in terms of molar ratio by converting an GC area ratio into a molar ratio, all temperatures are expressed in centigrade, and all pressures are in atmospheres (atm) unless otherwise indicated. The amount of tars is calculated as an amount of $C_2$ compounds by converting the total amount of compounds having at least 4 carbon atoms into that of $C_2$ compounds.

EXAMPLE 1

A 300 cc reaction vessel made of SS-316, equipped with a fractional distillation column, was used. Into the vessel, 133.4 g (1 mole) of 1,1,1-trichloroethane, 120 g (6 mole) of hydrogen fluoride, and 30 g (0.3 mole) of HCFC-142b were simultaneously fed. The resulting mixture was reacted at 100° C. for 1 hr. The reaction mixture was stirred by means of a magnetic bar stirrer. A refrigerant of −40° C. was introduced into a condenser provided on the top of the vessel in order to maintain the reaction pressure at 10 atm. At this time, the hydrogen chloride produced was removed through the condenser under the conditions that no organic substances arrived at the upper zone of the fractional distillation column. The reaction mixture was collected into an aqueous 20.7 wt % hydrogen chloride solution cooled to −50° C. through a valve in the bottom of the vessel, and analyzed by gas chromatography. The results are shown in Table 1 below.

COMPARATIVE EXAMPLES 1-2

The same reaction procedures as described in Example 1 were carried out by using the same reaction vessel under the same reaction conditions, except without feeding HCFC-142b into the vessel. Only 133.4 g of 1,1,1-trichloroethane was reacted with 120 g (6 mole) of hydrogen fluoride for 1 hr at 100° C., respectively. The results are shown in Table 1 below.

EXAMPLES 2-5

The same reaction procedures as described in Example 1 were carried out by using the same reaction vessel under the same reaction conditions, but while varying the reaction temperatures as shown in Table 1. The results are shown in Table 1 below.

TABLE 1

| Example | Temperature (°C.) | Molar ratio of 142b/MCF | Molar ratio of HF/MCF | Conversion of MCF (%) | Composition of the products (mole %)* | | | | |
|---|---|---|---|---|---|---|---|---|---|
| | | | | | MCF | R-141b | R-142b | R-143a | Tar |
| Ex. 1 | 100 | 0.3 | 6 | 87.6 | 9.5 | 60.2 | 30.0 | 0.2 | 0.1 |
| Comp. 1 | 100 | 0 | 6 | 72.5 | 27.5 | 58.7 | 8.4 | 0.1 | 5.3 |
| Comp. 2 | 120 | 0 | 6 | 87.3 | 12.7 | 51.8 | 27.4 | 1.1 | 7.0 |
| Ex. 2 | 50 | 0.3 | 6 | 11.4 | 68.2 | 8.8 | 23.0 | 0 | 0 |
| Ex. 3 | 80 | 0.3 | 6 | 56.8 | 33.3 | 40.3 | 26.4 | 0 | 0 |
| Ex. 4 | 120 | 0.3 | 6 | 92.3 | 5.9 | 37.6 | 53.8 | 1.8 | 0.9 |
| Ex. 5 | 150 | 0.3 | 6 | 99.0 | 0.8 | 15.5 | 74.1 | 8.5 | 1.2 |

*MCF: Methylchloroform ($CH_3CCl_3$)
R-141b: $CH_3CCl_2F$
R-142b: $CH_3CClF_2$
R-143a: $CH_3CF_3$

EXAMPLES 6-8

The same reaction procedures as described in Example 1 were carried out at 100° C., but while varying the amounts of hydrogen fluoride to be added. The results are shown in Table 2 below.

EXAMPLES 9-11

The same reaction procedures as described in Example 1 were carried out at 100° C., but while varying the amounts of HCFC-142b to be added with respect to 1,1,1-trichloroethane. The results are shown in Table 2 below.

TABLE 2

| Example | Pressure (atm.) | Molar ratio of 142b/MCF | Molar ratio of HF/MCF | Conversion of MCF (%) | Composition of the products (mole %)* | | | | |
|---|---|---|---|---|---|---|---|---|---|
| | | | | | MCF | R-141b | R-142b | R-143a | Tar |
| 6 | 10 | 0.3 | 2 | 65.4 | 26.6 | 44.0 | 29.2 | 0 | 0.2 |
| 7 | 12 | 0.3 | 4 | 79.2 | 16.0 | 52.9 | 30.9 | 0.1 | 0.1 |
| 8 | 15 | 0.3 | 8 | 91.3 | 6.7 | 58.2 | 34.8 | 0.3 | 0 |
| 9 | 8 | 0.2 | 6 | 79.5 | 17.9 | 58.6 | 23.2 | 0.1 | 0.2 |
| 10 | 20 | 0.4 | 6 | 92.5 | 5.4 | 55.8 | 37.7 | 1.1 | 0 |
| 11 | 20 | 0.6 | 6 | 97.5 | 1.6 | 49.0 | 47.9 | 1.5 | 0 |

*MCF: Methylchloroform ($CH_3CCl_3$)
R-141b: $CH_3CCl_2F$
R-142b: $CH_3CClF_2$
R-143a: $CH_3CF_3$

EXAMPLE 12 (CONTINUOUS REACTION PROCEDURE)

A 700 ml high-pressure reaction vessel was used. Into this vessel, 133.4 g (1 mole) of 1,1,1-trichloroethane, 120 g (6 mole) of hydrogen fluoride, and 30 g (0.3 mole) of HCFC-142b were simultaneously fed. The resulting mixture was reacted at 100° C. for 1 hr while maintaining the reaction pressure at 10 atm. After completion of the reaction, 1,1,1-trichloroethane, hydrogen fluoride, and HCFC-142b were introduced into the vessel at the rate of 1 mole/hr, 6 mole/hr, and 0.3 mole/hr, respectively. In order to maintain the reaction pressure at 10 atm, the hydrogen chloride produced was exhausted through the condenser in which a refrigerant of −40° C. was being cycled. The reaction product was continuously removed from the bottom of the vessel so that a constant liquid level in the vessel was maintained. After completion of the overall 10 hr reaction, the collected organic product was subjected to gas chromatography.

Yield: 1,343 g,

Composition of the product: MCF: 16.9%, R-141b: 46.6%, R-142b: 36.2%, R-143a: 0.1%, Tar: 0.2%.

What is claimed is:

1. A process for preparing 1,1-dichloro-1-fluoroethane and 1,1-difluoro-1-chloroethane from a reaction system composed of 1,1,1-trichloroethane and hydrogen fluoride in the absence of a catalyst, which comprises carrying out the reaction in the presence of 1,1-difluoro-1-chloroethane which is present at the beginning of the reaction at a molar ratio relative to 1,1,1-trichloroethane at or above 0.2.

2. The process of claim 1, wherein the molar ratio of said hydrogen fluoride to said 1,1,1-trichloroethane ranges from 3 to 8.

3. The process of claim 1, wherein said reaction is carried out at a temperature ranging from 70° to 120° C.

4. The process of claim 1, wherein the reaction pressure ranges from 6 to 15 atm.

5. The process of claim 1, wherein said process further comprises the steps of removing hydrogen chloride from the top of the reaction vessel, recovering continuously the reaction mixture from the bottom of the vessel, separating 1,1-dichloro-1-fluoroethane and 1,1-difluoro-1-chloroethane from the mixture, and recycling the unreacted reactants and an effective amount of 1,1-difluoro-1-chloroethane into the vessel.

* * * * *